(12) United States Patent  (10) Patent No.: US 7,406,152 B2
Teramoto et al.  (45) Date of Patent: Jul. 29, 2008

(54) X-RAY INSPECTION APPARATUS, X-RAY INSPECTION METHOD, AND X-RAY INSPECTION PROGRAM

(75) Inventors: Atsushi Teramoto, Kuwana (JP); Takayuki Murakoshi, Kuwana (JP)

(73) Assignee: Nagoya Electric Works Co., Ltd., Nagoya (JP)

( * ) Notice: Subject to any disclaimer, the term of this patent is extended or adjusted under 35 U.S.C. 154(b) by 331 days.

(21) Appl. No.: 11/288,474

(22) Filed: Nov. 29, 2005

(65) Prior Publication Data

US 2008/0043908 A1   Feb. 21, 2008

(30) Foreign Application Priority Data

Nov. 30, 2004   (JP)   ............... 2004-346182

(51) Int. Cl.
    *G01N 23/02*   (2006.01)
(52) U.S. Cl. ............... 378/58; 378/57; 378/62
(58) Field of Classification Search .......... 378/57, 378/58, 62, 63
    See application file for complete search history.

(56) References Cited

U.S. PATENT DOCUMENTS 6,028,910 A   2/2000   Kirchner et al.

6,335,957 B1   1/2002   DiBianca
6,763,083 B2 *   7/2004   Fernandez .......... 378/41

FOREIGN PATENT DOCUMENTS

JP   06-237077   8/1994
JP   11-174001   7/1999
JP   2000-356606   12/2000

OTHER PUBLICATIONS

Communication dated Feb. 28, 2006, including European Search Report dated Feb. 17, 2006 (total 6 pages).

* cited by examiner

*Primary Examiner*—Jurie Yun
(74) *Attorney, Agent, or Firm*—Oliff & Berridge, PLC

(57) ABSTRACT

In an inspection of an object of inspection with use of X-rays, X-rays are output from an X-ray source disposed fixedly into a range of a predetermined solid angle and, while the object of inspection is moved along a plane within the output range of the X-rays, the X-rays are detected, in positions included in the solid angle and at a plurality of revolved points around an axis oriented vertical to the plane along which the object of inspection is moved, with its detecting surface tilted down toward the axis. Thus, the object can be inspected based on the detected X-rays.

17 Claims, 5 Drawing Sheets

X-RAY INSPECTION APPARATUS, X-RAY INSPECTION METHOD, AND X-RAY INSPECTION PROGRAM

BACKGROUND OF THE INVENTION

1. Field of the Invention

The present invention relates to an X-ray inspection apparatus, an X-ray inspection method, and an X-ray inspection program.

2. Background Art

Conventionally, it has been practiced to apply X-rays to an object of inspection and analyze a transmission image thereby obtained and make a pass/fail test or the like of the inspection object (refer for example to patent document 1) In this document, there are disclosed such a technique as to dispose a θ-table on an X-Y stage and allow an X-ray source and a camera to tilt within a plane perpendicular to the X-Y stage (patent document 1, FIG. 1) and a technique to allow an X-ray source and a camera to revolve around an axis vertical to the X-Y stage (patent document 1, FIG. 2).

[PATENT DOCUMENT 1] Japanese Patent Unexamined Publication No. 2000-356606

SUMMARY OF THE INVENTION

With an X-ray inspection apparatus of a conventional art as mentioned above, it has been difficult to perform inspection of a great number of inspection objects at high speeds. More specifically, since an X-ray source uses a high voltage to generate X-rays, the apparatus becomes large and heavy. In order to move such a large and heavy X-ray source as in the conventional art example just mentioned above, a large-scaled mechanism is required and, in addition, much time is required to finish a movement. Especially when the object of inspection is such a small part as a BGA (Ball Grid Array) of an IC chip, it is required to locate the inspection object accurately at a right inspection position. However, it is very difficult to move the large and heavy mechanism to perform the position control with high precision and, further, it takes a long time.

Further, with an arrangement in which a θ-table is disposed on an X-Y stage, the mechanism for moving such an arrangement becomes larger in scale than in an arrangement in which only the X-Y stage is moved. Accordingly, even in this arrangement, a long time is taken in finishing the movement. Furthermore, it has been quite difficult to perform an inspection of small parts at high speeds because the degree of freedom in movement becomes high and, hence, high precision control becomes difficult.

In a case where total inspection of every part is carried out, capability of performing high precision control at high speeds has a great significance. More specifically, performing only sampling inspection is not sufficient with some vehicle-mounted parts and the like, and, therefore, with those products requiring total inspection, the production efficiency will be greatly reduced unless the inspection objects can be inspected at high speeds.

The present invention is made in view of the above mentioned problem and addresses the provision of an X-ray inspection apparatus, an X-ray inspection method, and an X-ray inspection program capable of inspecting a great number of inspection objects at high speeds.

To achieve the above mentioned object, one aspect of the invention is adapted such that an X-ray source is disposed in a position capable of outputting X-rays into a range of a predetermined solid angle and X-ray images of an object of inspection are taken with the inspection object moved along a plane within the solid angle. More particularly, while the X-ray source is fixedly disposed to be immovable, the directions in which the X-rays are emitted cover the predetermined solid angle. Accordingly, the X-ray inspection device is enabled to detect the X-rays in a plurality of positions included in the solid angle and, hence, a plurality of X-ray images can be obtained without the need for moving the large and heavy X-ray source and the inspection of objects can be conducted at high speeds.

In order to obtain large amounts of information from an object of inspection, e.g., to obtain a three-dimensional structure of the inspection object, for example, it is necessary to obtain X-ray images of the inspection object by applying X-rays to it from different angles. However, in the present invention, the inspection object is not rotated. That is, since X-ray images at a plurality of rotational positions can be obtained by means of the X-ray detector, the inspection object itself is not required to be rotated with respect to any axis. Thus, inspection of the objects can be conducted through only moving the inspection object with use of a simple arrangement and, even when a large number of inspection objects are to be inspected, the inspecting process can be performed at high speeds.

Here, an X-ray output device is only required to be fixedly disposed and able to emit X-rays into a range of a predetermined solid angle. The X-ray source is only required to be arranged immovable in inspecting objects of inspection. That is, when the X-ray inspection apparatus is installed in a factory, for example, it may only be installed so as not to move relative to the floor or the inspection line. Further, the range into which the X-rays are emitted is only required to be a range including the detecting surfaces placed at a plurality of rotational positions of the X-ray detector. That is, it is only required that the need for changing the angle of X-ray emission or moving the X-ray source in taking X-ray images in the plurality of rotational positions is eliminated by use of an X-ray tube capable of emitting X-rays in a wide range, instead of conventional X-ray tubes restricted in the range of X-ray emission.

As such an X-ray source, a transmission-type open tube may, for example, be used. More specifically, in the use of a transmission-type open tube, x-rays are radiated by a beam of electrons impinging on a thin target and when the X-rays are transmitted through the target and output to the outside, the range of emission covers substantially all directions (a solid angle of $2\pi$). Of course, inmost cases, the range of emission for taking images of inspection objects needs not be as large as $2\pi$. Rather, it is sufficient if an X-ray source capable of emitting X-rays into a solid angle covering at least the above mentioned plurality of rotational positions is used. However, the larger the solid angle, the greater becomes the number of types of the inspection objects to which the present invention is applicable. Then, the versatility of the present invention will be enhanced.

A planar movement mechanism is only required to be able to give a two-dimensional movement to an inspection object and it can be provided by a so-called X-Y stage or the like. Since it is not necessary to rotate the inspection object in the present invention, it is possible to bring the X-ray source close to the inspection object. Accordingly, an X-ray image with a high magnification factor can be easily obtained at the detecting surface of the X-ray detector and it is made possible to perform a highly precise inspection.

In the X-ray detector, it is only required that beams of X-rays output from the X-ray output device and beams of X-rays transmitted through an inspection object at a plurality of rotational positions can be obtained at the detecting surface of the detector. It is, for example, possible to employ, as the detector, a sensor which measures strengths of X-rays with a CCD in a two-dimensional array. Since, in this way, the X-rays are detected by the detector on the detecting surface with a predetermined area, such high precision, as demanded in the case where the inspection object is rotated, is not demanded of the positional accuracy of the rotational positions.

More specifically, since the detecting surface has a predetermined area, it can be arranged so that the image of an inspection object in the transmission X-ray image may not occupy the total range of the detecting surface but may leave certain margins at the top and bottom, and the left and right, of the detecting surface. Then, even if the position of the detecting surface is deviated somewhat in the rotational direction, it is made possible to obtain the X-ray image. However, while the inspection object is located close to the X-ray source to secure a high magnification power, the X-ray image after magnification, in the case where the inspection object is rotated, will be greatly affected even if the inspection object is deviated slightly from its right position.

Therefore, as compared with the case where the inspection object is rotated, a lower degree of positional accuracy is demanded of the rotational position in the X-ray detector of the present invention. Accordingly, an apparatus driven at high speeds can be easily designed. This feature of the arrangement of the present invention is specifically significant when a rotational mechanism for rotating the detecting surface, to be discussed later, is structured. More specifically, when the detecting surface is rotated to be positioned at a rotational position, not so high accuracy is demanded of the positioning. Therefore, the rotational operation can be finished at high speeds and high speed inspection can be performed.

The plurality of rotational positions may be such that are taken by the detecting surface when it is supposed to revolve around an axis vertical to the plane along which the object of inspection is moved. For example, taking, as the axis, a straight line connecting the focus of the X-ray source and the center of the range into which the X-rays are emitted, the rotational positions may be supposed to be on a circumference of a circle with a predetermined radius around the axis. Of course, the detecting surface detects X-rays in its attitude tilted down toward the axis, the tilt angle is determined such that the detecting surface faces the focus of the X-ray source.

In order to detect X-rays in a plurality of positions, various types of X-ray detector can be adopted. For example, a plurality of detectors having a tilted detecting surface as stated above may be used, or a rotational mechanism for causing a detector having the detecting surface as stated above to revolve around the axis may be used. In the case where a plurality of detectors are used, by previously disposing the plurality of detectors in all of the detecting positions, the inspection of the object of inspection can be conducted without moving any detectors and thus the inspection can be carried out at very high speeds.

On the other hand, a plurality of detectors or one detector may be revolved so as to detect X-rays at a plurality of rotational positions. This revolution is more simply controlled than in the combination of the X-Y stage and the θ-table as described above. Further, the planar transport movement in the planar movement mechanism and the rotational movement in the X-ray detector can be controlled individually and the planar transport movement and the rotational movement can be made simultaneously, and therefore, the overall moving operation can be completed at high speeds. Incidentally, when a plurality of detectors are revolved, the number of revolving operations can be made smaller than when one detector is revolved. Therefore, an advantage can then be obtained in the point of the accuracy and speed of the revolving operation.

The inspection object inspection device is only required to be able to conduct the inspection of the object of inspection depending on the detected X-rays. For example, the sectional area, volume, and shape of the object of inspection may be inspected or inspection as to whether a bridge is present or absent therein may be made depending on a plurality of transmission images and, further, by making reconstructing calculation based on a plurality of transmission images, tomograms may be obtained through calculation and a pass/fail test of soldering and the like may be performed.

Since, in the present invention, an arrangement enabling a high-speed inspection is employed as described above, it is preferred that such a layout as to carry out inline inspections is arranged in an inspection line of a workshop or the like. Then, by providing the planar movement mechanism with a conveyance mechanism capable of conveying a plurality of objects of inspection in succession to the range of X-ray emission, it becomes possible to inspect a plurality of inspection objects by inline processing. As a consequence, an X-ray detection apparatus advantageously applicable to objects of inspection requiring a total inspection can be provided.

In the present invention, by making an arrangement capable of moving an object of inspection to a desired position on a plane by use of the above described planar movement mechanism, the object of inspection can be disposed at a predetermined position for image taking (for example, on the straight line connecting the focus of the X-ray output device with the above referred predetermined position on the detecting surface). At this time, such an arrangement as to dispose the object of inspection at more precise position may be adopted. More specifically, if the relative positional relationship between the focus of the X-ray output device and the object of inspection is detected by means of a position sensor, the movement amount required for moving the object of inspection to the position on the straight line connecting the focus and the predetermined position on the inspection, as well as the coordinate of the predetermined position, can be calculated accurately.

Therefore, an accurate movement can be attained by the planar movement mechanism. Here, the position sensor is only required to be able to detect the relative positional relationship between the focus of the X-ray output device and the object of inspection. The relative positional relationship may, for example, be detected based on the distance (height) along the axis extended upward in the vertical direction from the focus. Of course, here, instead of using such an arrangement directly detecting the relative positional relationship between the object of inspection and the focus, the relative positional relationship between the substrate or the like with the object of inspection mounted thereon and the focus may be detected and the relative positional relationship having the thickness of the substrate or the like taken into consideration may be obtained, or it may also be considered that the thickness of the substrate or the like is negligible.

In the foregoing, cases where the present invention is realized as apparatuses have been described. The present invention is also applicable to a method for realizing such apparatuses. As an example, the invention could be constituted as a method to realize the arrangement set forth. Of course, the operation in the method is substantially equal to that in the described apparatus. Methods for arrangements corresponding to the above mentioned variation are also possible. Such X-ray detecting apparatuses may be realized individually, may be applied to a method, or such a method may be utilized as incorporated in another apparatus. Thus, thoughts of the invention are not limited to such as described above but may include various modifications. Thus they can be suitably modified as software in one instance and as hardware in the other instance.

When the invention is used as software for controlling the above method, as an example of the realization of the thought of the invention, the thought naturally exists and is used in such software, or a recording medium having such software recorded thereon. For example, the invention could be stated as a constitution realizing the functions set forth by software. Of course, software corresponding to each of the above mentioned variation may also be constituted.

Further, the recording media of software may be magnetic recording media or magnetooptical recording media. Identical way of thinking may be made for any recording media to be developed in future. It is beyond controversy that the thought is also applicable to duplicated products, such as primary duplicate and secondary duplicate. The present invention is doubtlessly utilized when a communication circuit is used as a resource. Further, in a case where the thought is realized partly as software and partly as hardware, it is not completely different from that of the invention. The apparatus may also be of such an arrangement in which a portion of data is stored on a recording medium and the data is read out as needed.

DETAILED DESCRIPTION OF THE PREFERRED EMBODIMENTS

Figure 1:
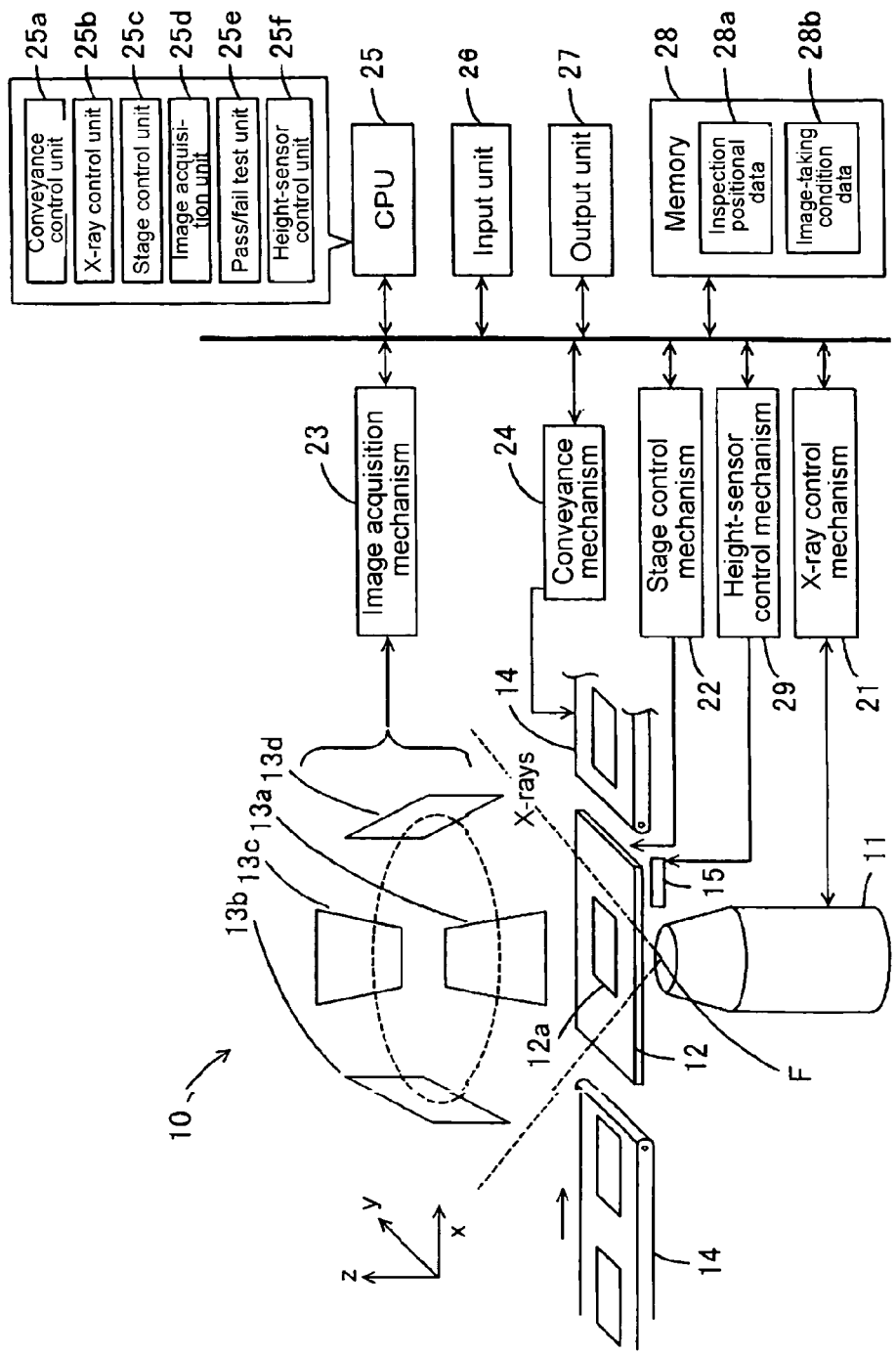
FIG. 1 is a schematic block diagram of an X-ray detection apparatus according to the present invention.

An embodiment of the present invention will be described in the sequential order as follows:
(1) Arrangement of the present invention;
(2) X-ray detection process; and
(3) Other embodiments.
(1) Arrangement of the Present Invention:

FIG. 1 is a schematic block diagram of an X-ray inspection apparatus 10 according to a first embodiment of the present invention. Referring to FIG. 1, the X-ray inspection apparatus 10 includes an X-ray generator 11, an X-Y stage 12, X-ray detectors 13a-13d, and a conveyor 14, each thereof being controlled by a CPU 25. More specifically, the X-ray inspection apparatus 10, as a control system including the CPU 25, is made up of an X-ray control mechanism 21, a stage control mechanism 22, an image acquisition mechanism 23, a conveyance mechanism 24, the CPU 25, an input unit 26, an output unit 27, a memory 28, and a height-sensor control mechanism 29. In the above mentioned arrangement, the CPU 25 is capable of executing programs, not shown, stored in the memory 28 thereby controlling each unit and also performing predetermined arithmetic processing. Further, a planar movement mechanism consists of the X-Y stage 12 and the stage control mechanism 22.

The memory 28 is a storage medium capable of storing data, in which there are previously stored inspection positional data 28a and image-taking condition data 28b. The inspection positional data 28a is data indicating the position of an object of inspection, i.e., in the present embodiment, data indicating the position of a BGA disposed on a substrate. The image-taking condition data 28b is data for indicating the conditions on which X-rays are generated by the X-ray generator 11, including such as the voltage applied to the X-ray tube, the image-taking time, and the like. The memory 28 is only required to be capable of storing data, and various storage media such as RAM, EEPROM, HDD, and the like can be used therefor.

The X-ray control mechanism 21 is enabled, by referring to the image-taking condition data 28b, to control the X-ray generator 11 so that X-rays on predetermined conditions are generated. The X-ray generator 11 is a so-called transmission type open tube and the same can emit X-rays from a focus F as the X-ray emitting position into all directions, i.e., into the range of a solid angle of $2\pi$. The X-ray generator 11 is disposed fixedly with respect to the X-ray inspection apparatus 10, i.e., the X-ray generator 11 suffers no change in its position or angle and immovable as fixed to the apparatus.

The stage control mechanism 22 is connected with the X-Y stage 12 and controls the X-Y stage 12 in accordance with the inspection positional data 28a. The conveyance mechanism 24 controls the conveyor 14 so that a substrate 12a is conveyed onto the X-Y stage 12. More specifically, the conveyance mechanism 24 is adapted to consecutively make such operations as to convey the substrate 12a in one direction with use of the conveyor 14, and after the BGA placed on the substrate 12a is inspected on the X-Y stage 12, to remove the substrate 12a gone through the inspection process with the conveyor 14.

Incidentally, the position of the BGA on the substrate 12a is specified by the inspection positional data 28a as described above and the stage control mechanism 22, during the course of inspection of the BGA, perform control such that the BGA is located in the center of the field of view of the x-ray detector 13a-13d. Namely, the position of the BGA is changed a plurality of times such that the BGA comes to be located on a straight line connecting the focus F of the X-ray generator 11 with the center of the detecting surface of the X-ray detector 13a-13d and an X-ray image is taken in each position.

The image acquisition mechanism 23 is connected with the X-ray detectors 13a-13d and acquires projected images of the object of inspection according to the detected values output from the X-ray detectors 13a-13d. The X-ray detector 13a-13d according to the present embodiment has a sensor in a two-dimensional array and is thereby enabled to generate X-ray image data indicating a two-dimensional distribution of the X-rays from the detected X-rays.

The height-sensor control mechanism 29 is connected with a height sensor 15 and it obtains, according to the inspection positional data 28a, the height of the BGA as the object of inspection, i.e., the distance in the vertical direction from the focus F of the X-ray generator 11 to the BGA. The height sensor 15 is only required to be a sensor capable of detecting the distance and therefore one selected from various types of sensors may be used therefor.

The output unit 27 is a display for displaying thereon the X-ray image or the like obtained by the process of the CPU 25 and the input unit 26 is an operating input unit for accepting user's inputs. Namely, the user is enabled to have various inputs to be executed through the input unit 26. Various results of calculation, X-ray image data, results of the pass/fail test of the objects of inspection, and the like can be displayed on the output unit 27.

The CPU 25 is able to perform predetermined computing processing according to various control programs stored in the memory 28 and, in order to inspect an object of inspection, executes calculations in a conveyance control unit 25a, X-ray control unit 25b, stage control unit 25c, image acquisition unit 25d, pass/fail test unit 25e, and a height-sensor control unit 25f shown in FIG. 1. The conveyance control unit 25a controls the drive of the conveyor 14 to feed the substrate 12a to the X-Y stage 12 at suitable timing and also removes the substrate 12a gone through the inspection from the substrate 12a at suitable timing.

The X-ray control unit 25b, retrieving the image-taking condition data 28b, controls the X-ray control mechanism 21 so that specified X-rays are output from the X-ray generator 11. The height-sensor control unit 25f, retrieving the inspection positional data 28a, specifies a BGA as an object of inspection and indicates the position of the BGA to the height-sensor control mechanism 29. Thereupon, the height-sensor control mechanism 29 controls the height sensor 15 to obtain the distance in the vertical direction from the focus F of the X-ray generator 11 to the BGA.

The stage control unit 25c, acquiring the inspection positional data 28a, calculates the coordinate values for moving the BGA as the object of inspection to the plurality of centers of the field of view and supplies the calculated values to the stage control mechanism 22. As a result, the stage control mechanism 22 moves the X-Y stage 12 such that the coordinate is brought over the focus F in the vertical direction to allow the BGA to take a suitable position. Details of this processing will be described later on. The image acquisition unit 25d records the X-ray image data acquired by the image acquisition mechanism 23 in the memory 28. The pass/fail test unit 25e performs predetermined computational processing on the basis of the recorded X-ray image data and determines whether the object of inspection is good or bad.

Figure 2:
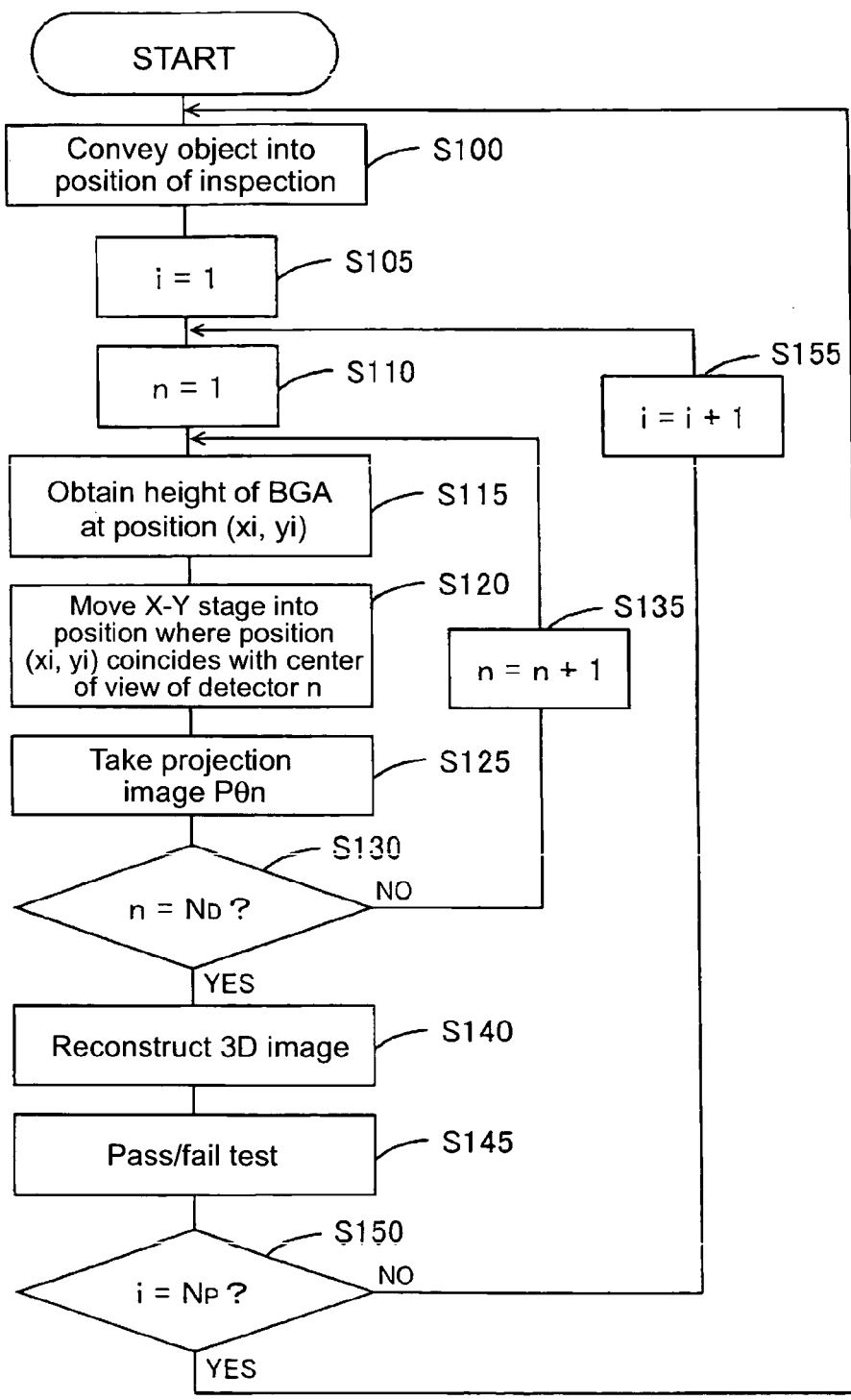
FIG. 2 is a flowchart of an X-ray detection process.

(2) X-Ray Detection Process:

In the present embodiment, a pass/fail test is performed in the above described arrangement following the steps in the flowchart shown in FIG. 2. In the present embodiment, a plurality of substrates 12a are conveyed by the conveyor 14 and the BGAs are inspected in succession on the substrate 12a brought onto the X-Y stage 12. To achieve this, in the execution of inspection, the conveyance control unit 25a first gives an instruction to the conveyance mechanism 24 in step S100 so that a substrate 12a is conveyed by the conveyor 14 onto the X-Y stage 12.

Then, the stage control unit 25c, in order to move the BGA as the object of inspection to a suitable position, initializes the variables i and n to "1" (step S105, S110). In the present embodiment, $N_P$ pieces of the BGAs are used as the objects of inspection and the variable i, taking values 1 to $N_P$, represents the number allocated in advance to the BGA to be placed on the substrate. On the other hand, the variable n indicates the number of positions where an X-ray image is taken, of which the number $N_D$ is the maximum value. Since a total of four X-ray detectors 13a-13d are employed in the present embodiment, i.e., X-ray images are taken at four positions, the variable n takes values "1"-"4".

In succession to the above, the height-sensor control unit 25f acquires the inspection positional data 28a in step S115 and indicates the coordinate of the i-th BGA $(x_i, y_i)$ to the height-sensor control mechanism 29. As a consequence, the distance between the BGA at the coordinate $(x_i, y_i)$ and the focus F of the X-ray generator 11 in the vertical direction is output from the height sensor 15 and the height-sensor control unit 25f records this height as an FOD in the memory 28.

Figure 3:
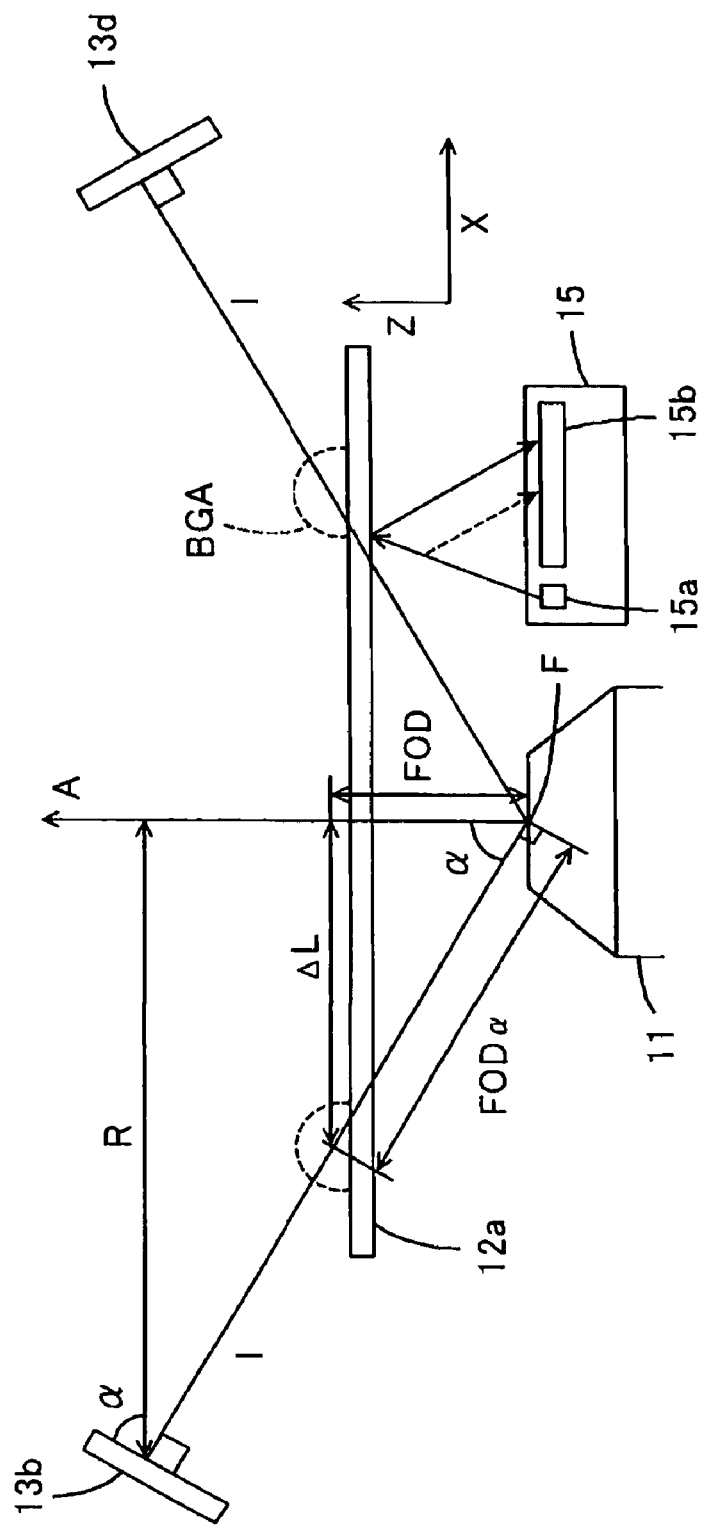
FIG. 3 is a diagram explanatory of the arrangement of the X-ray detection apparatus in connection with a coordinate system.

In FIG. 3, there is shown the height sensor 15 according to the present embodiment. The height sensor 15 is disposed below the substrate 12a and provided with a laser emitter 15a and a line sensor 15b. The laser emitter 15a is capable of emitting a laser beam toward the substrate 12a and the line sensor 15b is a sensor for detecting the laser beam reflected from the substrate 12a. The line sensor 15b is provided with a plurality of sensors in an array in a direction, in which the direction along which the line sensors are aligned and the horizontal component of the emitted direction of the laser beam are in agreement.

Therefore, according as the reflected laser beam is moved following the movement of the substrate 12a in the vertical direction, the position of the line sensor 15b at which the reflected laser beam arrives also moves (for example, when the substrate 12a is moved downward, the locus of the laser beam moves from that shown by the continuous line to that shown by the broken line). Therefore, the height-sensor control unit 25f takes the position, at which the reflected laser beam detected by the line sensor 15b exhibits its maximum brightness, as the position of arrival of the reflected laser beam and, based on this position of arrival, detects the height of the BGA. Incidentally, by geographically analyzing the optical path of the laser beam, the distance in the vertical direction between the bottom surface of the substrate 12a and the focus F can be calculated. Then, by taking the thickness of the substrate 12a and the height from the top surface of the substrate 12a to the center of the BGA into consideration, the height from the focus F to the center of the BGA can be calculated. Thus, this height may be set as the FOD.

Of course, if the height from the top surface of the substrate 12a to the center of the BGA and the thickness of the substrate 12a are very small, the FOD may be defined by neglecting these values. Even if these values are neglected, when the degree of the change in position of the substrate 12a in the vertical direction is greater than the thickness of the substrate 12a and the height from the top surface of the substrate 12a to the center of the BGA, an FOD accurate enough to secure the positional precision of the BGA can be obtained.

Further, the stage control unit 25c acquires the inspection positional data 28a in step S120 and indicates, to the stage control mechanism 22, the coordinate values for bringing the coordinate $(x_i, y_i)$ of the i-th BGA to the center of the field of view of the X-ray detectors 13a-13d corresponding to the variable n, so that the X-Y stage 12 is moved accordingly. Incidentally, in the present embodiment, the values "1"-"4" of the variable n correspond to X-ray detectors 13a-13d, respectively. Further, in the present embodiment, the stage control mechanism 22 moves the X-Y stage 12 such that the given coordinate values come to a point vertically over the focus F of the X-ray generator 11. Such coordinate values are defined by a predetermined fixed coordinate system irrespective of the movement of the X-Y stage 12. The point into which the focus F of the X-ray generator 11 is projected when the X-Y stage 12 is in its initial position (in its unmoved state) is defined as the coordinate (0, 0).

Figure 4:
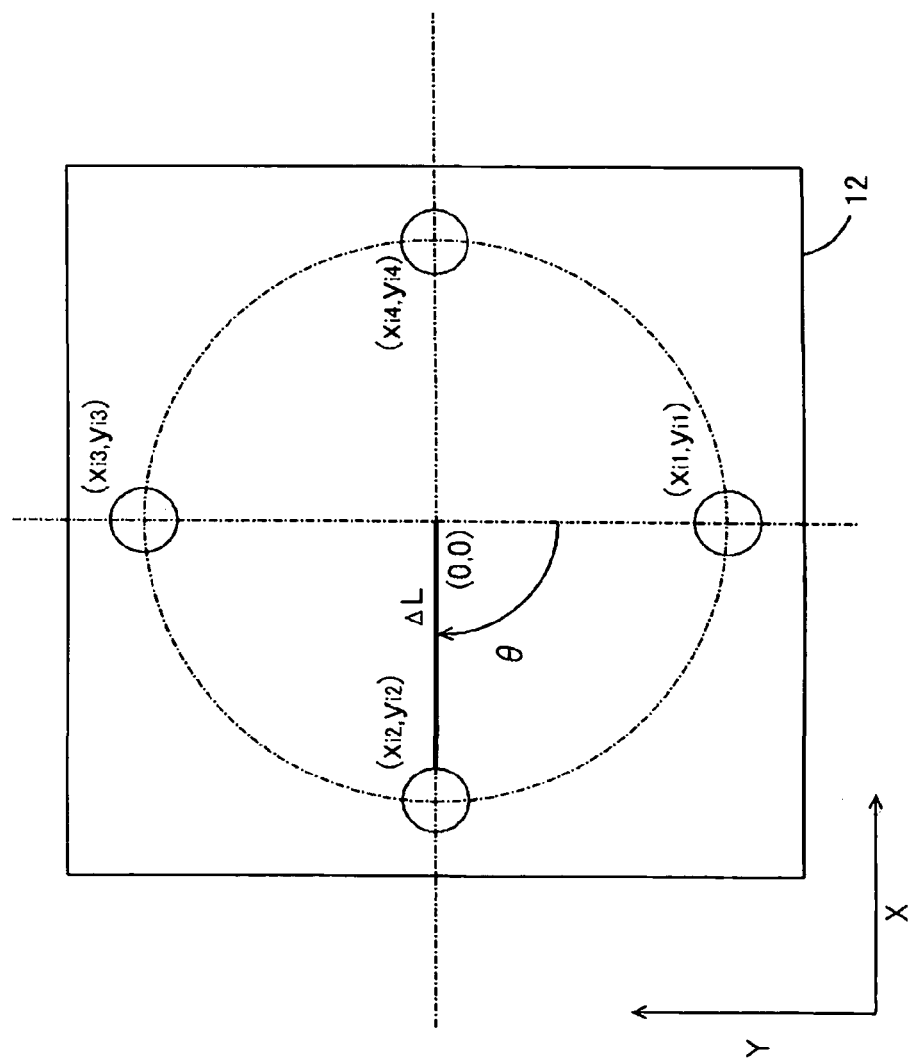
FIG. 4 is a diagram explanatory of the arrangement of the X-ray detection apparatus in connection with a coordinate system.

The above referred coordinate system is shown in FIG. 3 and FIG. 4. In these drawings, the plane along which the X-Y stage 12 moves is defined as an x-y plane and the direction vertical to the plane is defined as a z-direction. FIG. 3 is a diagram viewing the z-x plane and FIG. 4 is a diagram viewing the x-y plane. The above referred predetermined fixed coordinate system corresponds to the coordinates on the x-y plane shown in FIG. 4. In the present embodiment, the X-ray detectors 13a-13d are disposed such that the centers of their detecting surfaces are located on a circumference having a radius of R and having, as its center, an axis A connecting the focus F of the X-ray generator 11 with the coordinate (0, 0) in the fixed coordinate system.

Further, the detecting surface of each of the X-ray detectors 13a-13d is oriented perpendicular to the line 1 connecting the center of each detecting surface with the focus F. More specifically, the detecting surface is tilted down toward the axis A and a predetermined angle (tilt angle) of α is formed between the x-y plane and the detecting surface. Further, the X-ray detectors 13a-13d are distributed such that neighboring detectors are all at even intervals from each other. Accordingly, when it is assumed that the radius R connecting the axis A with the center of a detecting surface is rotated, then if the radius R is rotated 90° from the center of one detecting surface, it comes into agreement with the center of the neighboring detecting surface.

In a detecting surface arranged as described above, the center of the field of view agrees with the above mentioned straight line 1. In taking an X-ray image of the object, the object of inspection is disposed at the intersection of the straight line 1 with the x-y plane. In FIG. 4, the positions of the centers of the fields of view in the above described fixed coordinate system are indicated by coordinates $(x_{i1}, y_{i1})$-$(x_{i4}, y_{i4})$. In the X-ray detectors 13a-13d, as described above, there is the center of a neighboring detecting surface present at the position to which one center of detecting surface is moved by one rotation of 90° of the radius R. Therefore, the intersections of the straight lines 1 with the x-y plane are also present on the predetermined circumference and angles θ between radiuses ΔL connecting the neighboring positions with the origin (0, 0) are 90° apart from each other.

The stage control unit 25c is only required to determine the above stated coordinate values such that the coordinates of the i-th BGA $(x_i, y_i)$ are located at $(x_{i1}, y_{i1})$-$(x_{i4}, y_{i4})$, and therefore, the unit 25c determines the coordinate values according to the following equations (1)-(4):

$$x_{oin} = x_i + \Delta L \cdot \sin \theta \quad (1)$$

$$y_{oin} = y_i + \Delta L \cdot \cos \theta \quad (2)$$

$$\Delta L = FOD_\alpha \cdot \sin \alpha \quad (3)$$

$$FOD_\alpha = FOD / \cos \alpha \quad (4)$$

Here, the coordinate $(x_{oin}, y_{oin})$ is the coordinate for moving the i-th BGA to the center of the field of view of the X-ray detector 13a-13d corresponding to the variable n. The angle θ is an angle established in a clockwise direction for the straight line connecting the origin (0, 0) with the coordinate $(x_{i1}, y_{i1})$ as shown in FIG. 4. In the present embodiment, this angle becomes 0°, 90°, 180°, and 270° for each of the coordinates $(x_{i1}, y_{i1})$-$(x_{i4}, y_{i4})$.

The FOD is the height measured by the height sensor 15 and is the distance between the i-th BGA and the focus F in the direction of the z-axis. The angle α is the above referred tilt angle and, on the basis of this value, $FOD_\alpha$ and ΔL are calculated from equations (3) and (4). By substituting these results and the angle θ into equations (1) and (2), the above coordinate values can be obtained. Since the transport of the X-Y stage 12 is controlled by making use of the height measured by the height sensor 15 in the present embodiment, it is achieved to dispose the BGA accurately in the center of the field of view.

The above coordinate $(x_{oin}, y_{oin})$ is such that is obtained by adding the amount indicating the differential from the origin to the coordinate $(x_{in}, y_{in})$, i.e., $\Delta L \cdot \sin \theta$ or $\Delta L \cdot \cos \theta$, to each element of the coordinate $(x_i, y_i)$ of the i-th BGA. Therefore, by controlling the position of the X-Y stage 12 such that the point of the coordinate $(x_{oin}, y_{oin})$ in the fixed coordinate system comes into agreement with the axis A, it is attained to dispose the i-th BGA in the center of the field of view of the X-ray detectors 13a-13d corresponding to the variable n. Of course, once the X-Y stage 12 has been moved, the X-Y stage 12 is displaced from its initial position. However, since the coordinate used here is that of the fixed coordinate system, the amount to move the X-Y stage 12 can be determined based on equations (1) and (2) no matter what value the variable n may be.

After the i-th BGA has been moved to the center of the field of view corresponding to the variable n in step S120 as described above, a projected image $P_{\theta n}$ is taken under the control of the X-ray control unit 25b and the image acquisition unit 25d. More particularly, the X-ray control unit 25b acquires the image-taking condition data 28b and gives instructions to the X-ray control mechanism 21 to output X-rays on the conditions indicated in the image-taking condition data 28b. As a result, the X-ray generator 11 outputs the X-rays within a solid angle of 2π, and therefore, the image acquisition unit 25d obtains an X-ray image detected by the X-ray detector 13a-13d corresponding to the variable n.

In step S130, it is determined whether or not the variable n has reached the maximum value $N_D$ of the image-taking position, and when it is determined that it has not yet reached the maximum value $N_D$, the value n is incremented in step S135 and thereafter the processes following step S115 are performed again. On the other hand, when it is determined that the variable n has reached the maximum value $N_D$, the pass/fail test unit 25e makes the pass/fail decision. It is adapted in the present embodiment such that a three-dimensional image of the BGA is produced on the basis of projected images at a plurality of positions and that the pass/fail decision is made based on this three-dimensional image.

To attain that, the pass/fail test unit 25e first performs a restructuring process of the three-dimensional image in step S140. More specifically, in the present embodiment, three-dimensional data of the object of inspection is reconstructed based on a plurality of X-ray images. In the present embodiment, it is only required of the reconstructing process that the object of inspection is reconstructed, for which various methods can be adopted. For example, a filtered back projection algorithm may be used. In this process, Fourier transform is applied to any one of n sets of X-ray images and a filter correction function is multiplied in frequency space to the result obtained by the Fourier transform. By further applying inverse Fourier transform to the obtained result, filter-corrected image can be obtained. Incidentally, as the filter correction function, such a function as that enhances the edge of image may be used.

Then, the image gone through the filer-correction is back-projected into three-dimensional space along its projected optical path. More specifically, since the optical path corresponding to an image in a position of the detecting surface of the X-ray detectors 13a-13d is the straight line connecting the focus F of the X-ray generator 11 with this position, the above referred image is back-projected on the straight line. If back-projecting operations as described above are performed on all of the n sets of X-ray images, distributions of the X-ray absorption coefficients of the portions where the object of inspection is present in the three-dimensional space are emphasized so that the three-dimensional shape of the object of inspection can be obtained. The described process is just an example. Namely, various processes can be employed, such that, for example, adds a process to increase the number of X-ray images in a pseudo manner by making interpolation between n sets of X-ray images.

After performing the reconstructing process in step S140, the pass/fail test unit 25e performs a pass/fail test process in step S145. Namely, since the three-dimensional image of the object of inspection is obtained, the unit checks the sectional area, volume, or shape of the object of inspection or existence or absence of a bridge in soldered portions or the like. Here, by previously setting up criterion threshold values for the sectional area, volume, or the like or by setting up a criterion shape or the like, the inspection can be automated. At this time, the pass/fail test unit 25e outputs the result of the pass/fail test to the output unit 27. The inspection may of course be carried out by visually inspecting the three-dimensional image. The reconstruction of a three-dimensional image is not essential but two-dimensional image may be reconstructed or appearance inspection may be made on the basis of n sets of X-ray image without making any reconstruction process.

After the pass/fail test in step S145 has been completed, it is determined whether the variable i has reached the maximum value $N_P$, and when it is determined that the variable i has not yet reached the maximum value $N_P$, the variable i is incremented in step S155 and processes following step S110 are repeated. When it is determined that the variable i has reached the maximum value $N_P$ in step S150, it is understood that a series of inspections has been generally completed on the objects of inspection brought onto the substrate. Therefore, the inline inspections of the objects of inspection are continued by repeating the processes following step S100.

Incidentally, there has been proposed a method in which projected images are taken with the X-Y stage 12 moved to the positions where individual BGAs as the objects of inspection are placed in the centers of the field of view of the detectors, whereupon a pass/fail test of the inspected object is performed. However, it may also be possible to take images of a plurality of BGAs for each detector n and store the taken images in a memory at first, and then, to construct the three-dimensional images of a plurality of BGAs from the stored images. In this case, moved distances of the X-Y stage 12 can be shortened.

In the present embodiment, as described above, the X-ray generator 11 is disposed fixedly and its position or angle is not changed. More specifically, by employing an X-ray generator 11 capable of outputting X-rays substantially in all directions (a solid angle of $2\pi$) and by using a plurality of X-ray detectors 13a-13d and an X-Y stage 12 in combination, it is attained to obtain X-ray images at a plurality of angles. Accordingly, the need for moving a large and heavy X-ray generator 11 can be eliminated and what is needed as the drive member for obtaining a plurality of X-ray images is only the X-Y stage 12. As a result, an object of inspection can be inspected at very high speeds and, by combining the above described arrangement with a mechanism capable of continuously conveying a plurality of objects of inspection, a plurality of objects of inspection can be inspected at high speeds.

Figure 5:
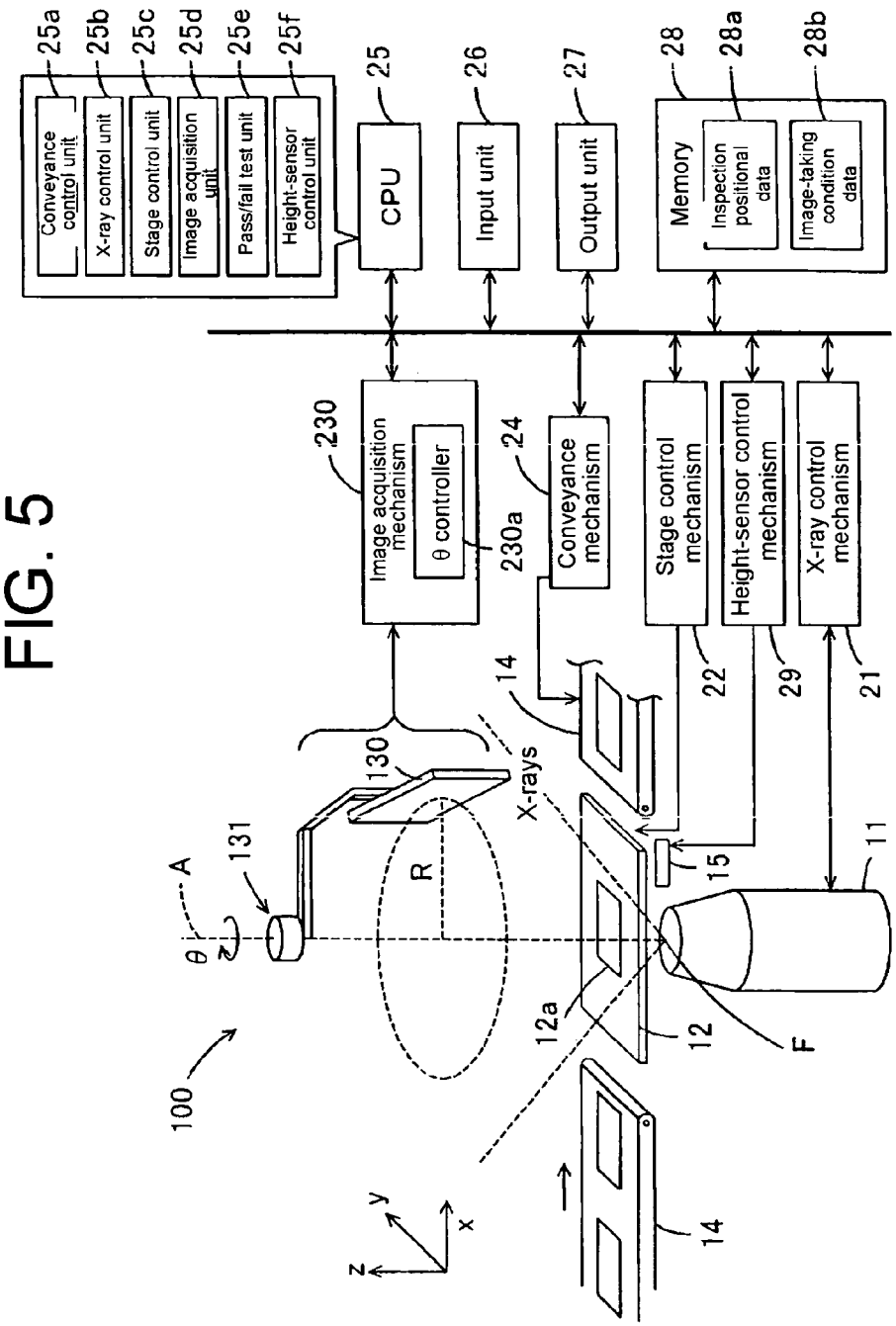
FIG. 5 is a schematic block diagram showing a second embodiment of the X-ray detection apparatus according to the present invention.

(3) Other Embodiments:

In the present invention, it is sufficient if X-ray images at a plurality of rotational positions can be obtained based on X-rays from a fixedly-disposed X-ray source. Other than the above described embodiment, various arrangements can be adopted. For example, an arrangement in which a rotational mechanism is provided for rotating an X-ray detector may be adopted. FIG. 5 is a schematic block diagram of an X-ray inspection apparatus 100 provided with such a rotational mechanism.

As shown in FIG. 5, the arrangement of the X-ray inspection apparatus 100 is in common with that of X-ray inspection apparatus 10 in many respects and such common components are denoted by the same reference marks as in FIG. 1. The X-ray inspection apparatus 100 shown in FIG. 5 has only one X-ray detector 130 and this X-ray detector 130 is connected with a rotational mechanism 131. The rotational mechanism 131 is capable of revolving the X-ray detector 130 around the axis A extended upward in the vertical direction from the focus F of the X-ray generator 11 and its revolution is controlled by a θ controller 230a of an image acquisition mechanism 230.

Also in the arrangement shown in FIG. 5, the X-ray detector 130 is tilted down toward the axis A by a tilt angle of α and the center of the X-ray detector 130 is capable of revolving around the axis A along the circumference of a circle with a radius of R. Further, the detecting surface of the X-ray detector 130 is included in the range of output X-rays from the X-ray generator 11. Therefore, the detecting surface of the X-ray detector 130 is enabled to take the same rotational positions as taken by the X-ray detectors 13a-13d in the earlier described embodiment.

In the above described arrangement, the image acquisition unit 25d gives instructions to the θ controller 230a, in synchronism with control instructions of X-Y stage 12 issued by the stage control unit 25c, to rotate the object of inspection so as to be located in the center of the field of view of the X-ray detector 130. For example, a rotational drive is made such that the object of inspection is located at the coordinate $(x_{i1}, y_{i1})$ as shown in FIG. 4 and the center of detecting surface of the X-ray detector 130 is positioned on the extension of the straight line connecting this position with the focus F of the X-ray generator 11.

Even when such an arrangement provided with the rotational mechanism 131 is used, the X-Y stage 12 becomes lighter than the arrangement in which a θ-table is disposed on the X-Y stage 12 and, therefore, the X-Y stage 12 can be rotated at high speeds. Further, since the rotational mechanism 131 can be simply controlled and the X-ray detector 130 can be structured of a light-weighing flat panel or the like, the rotation can be completed within a time equal to or shorter than in the movement of the object of inspection by the X-Y stage 12. Accordingly, an object of inspection can be inspected at very high speeds also when the arrangement shown in FIG. 5 is used, and by combining the above described arrangement with a mechanism capable of conveying objects of inspection continuously, a plurality of inspection objects can be inspected at high speeds.

Further, instead of using a plurality of X-ray images for reconstructing a three-dimensional image, those images may be used as individual transmission X-ray images taken from different angles for making a pass/fail test. For example, in place of step S140 and step S145 in FIG. 2, a pass/fail test process based on X-ray images $P_{\theta n}$ taken from different angles θ may be inserted. Incidentally, when each individual X-ray image is used for a pass/fail test, an appearance inspection based on the transmission X-ray image can be carried out. Therefore, such an arrangement may be made in which the fields of view of the X-ray image $P_{\theta n}$ are adjusted such that a plurality of BGAs are included in the fields of view to enable the plurality of BGAs to be inspected at one time. Since numbers of BGAs can be inspected by taking a small number of images in such an arrangement, it becomes possible to perform inspection at very high speeds.

What is claimed is:

1. An X-ray inspection apparatus comprising:
   an X-ray output device having a single X-ray source which is fixedly disposed, and which outputs X-rays into a range of a predetermined solid angle having an axis;
   a planar movement mechanism for moving an object of inspection along a plane within the range of the predetermined solid angle;
   an X-ray detector for detecting X-rays, in positions included in the predetermined solid angle and at at least three revolved points around the axis oriented perpendicular to the plane along which the object of inspection is moved, with its detecting surface tilted down toward the axis, the X-ray detector disposed above the X-ray source, wherein the X-ray detector detects the object of inspection in a plurality of object positions on the plane; and
   an object inspection device for inspecting the object of inspection based on the detected X-rays.

2. The X-ray inspection apparatus according to claim 1, wherein said X-ray detector includes a plurality of detectors having the detecting surface.

3. The X-ray inspection apparatus according to claim 1, wherein said X-ray detector includes a rotational mechanism for allowing the X-ray detector having the detecting surface to revolve around the axis.

4. The X-ray detection apparatus according to claim 1, wherein said object inspection device performs inspection of the object of inspection based on one or more of a transmission image and a tomogram of the object of inspection.

5. The X-ray inspection apparatus according to claim 1, wherein the planar movement mechanism is capable of moving the object of inspection along two or more substantially different dimensions.

6. The X-ray inspection apparatus according to claim 1, wherein:
   the X-ray detector comprises a plurality of detectors, each of the plurality of detectors not touching any other of the plurality of detectors, and each of the plurality of detectors spaced substantially apart to detect the object of inspection at the plurality of object positions on the plane.

7. The X-ray inspection apparatus according to claim 1, wherein:
   the X-ray detector comprises a single detector, and
   the X-ray inspection apparatus is configured to move the single detector around the axis into the positions, the positions spaced substantially apart, to detect the object of inspection at the plurality of object positions on the plane.

8. The X-ray inspection apparatus according to claim 1, wherein:
   the X-ray inspection apparatus detects the object of inspection in the plurality of object positions on the plane without rotating the object of inspection.

9. The X-ray inspection apparatus according to claim 1, further comprising a conveyance mechanism, wherein:
   the planar movement mechanism is an X-Y stage, and
   the X-ray inspection apparatus is configured to move the object of inspection onto the X-Y stage using the conveyance mechanism.

10. The X-ray inspection apparatus according to claim 1, wherein the X-ray inspection apparatus is configured to calculate a relative positional relationship between a focus of the X-ray inspection apparatus and the object of inspection.

11. The X-ray inspection apparatus according to claim 10, wherein the relative positional relationship is calculated based on a distance along a vertical direction between the focus of the X-ray inspection apparatus and a substrate on which the object of inspection is mounted.

12. The X-ray inspection apparatus according to claim 1, wherein:
   the plurality of object positions on the plane are located where the plane intersects with respective straight lines,
   the respective straight lines are substantially normal to the tilted detecting surface of the X-ray detector, and
   the respective straight lines extend from the X-ray detector to a focus of the X-ray inspection apparatus.

13. The X-ray inspection apparatus according to claim 1, wherein:
   the object of inspection is one of a plurality of objects of inspection, and
   the X-ray inspection apparatus is configured to detect each of the plurality of objects of inspection in the plurality of object positions on the plane by detecting each of the plurality of objects of inspection at one of the plurality of object positions on the plane before detecting each of the plurality of objects of inspection at another of the plurality of object positions on the plane.

14. A method of X-ray inspection for inspecting an object of inspection with X-rays which comprises:
   outputting X-rays from a single X-ray source, disposed fixedly, into a range of a predetermined solid angle having an axis;
   moving the object of inspection along a plane within the range of the predetermined solid angle;
   detecting X-rays, in positions included in the predetermined solid angle and at atleast three revolved points around the axis oriented perpendicular to the plane along which the object of inspection is moved, with its detecting surface tilted down toward the axis; wherein the detecting includes detecting the object of inspection in a plurality of object positions on the plane; and
   inspecting the object of inspection based on detected X-rays.

15. The method of X-ray inspection according to claim 14, further comprising moving the object of inspection along the plane along two or more substantially different dimensions.

16. A computer-readable medium encoded with a program of X-ray inspection for inspecting an object of inspection, the program instructing a device to perform functions comprising:
   an X-ray outputting function for controlling a single X-ray source disposed fixedly to output X-rays into a range of a predetermined solid angle having an axis;
   a planar-transport control function for controlling a planar transport mechanism to move the object of inspection along a plane within the range of the predetermined solid angle;
   an X-ray detection function for controlling detection of the X-rays, in positions included in the predetermined solid angle and at at least three revolved points around the axis oriented perpendicular to the plane along which the object of inspection is moved, with its detecting surface tilted down toward the axis; wherein the detecting function detects the object of inspection in a plurality of object positions on the planet; and
   an object inspecting function to inspect the object of inspection based on the detected X-rays, wherein the device performs all of the functions enumerated above.

17. The computer-readable medium encoded with a program of X-ray inspection according to claim 16, wherein the functions further comprise a second planar-transport control function to move the object of inspection along the plane along two or more substantially different dimensions.

* * * * *